(12) United States Patent
Biedermann et al.

(10) Patent No.: US 10,285,822 B2
(45) Date of Patent: May 14, 2019

(54) LENGTH ADJUSTABLE IMPLANT

(71) Applicant: Biedermann Technologies GmbH & Co. KG, Donaueschingen (DE)

(72) Inventors: Timo Biedermann, Trossingen (DE); Wilfried Matthis, Weisweil (DE)

(73) Assignee: BIEDERMANN TECHNOLOGIES GMBH & CO. KG, Donaueschingen (DE)

(*) Notice: Subject to any disclaimer, the term of this patent is extended or adjusted under 35 U.S.C. 154(b) by 792 days.

(21) Appl. No.: 14/624,444

(22) Filed: Feb. 17, 2015

(65) Prior Publication Data
US 2015/0230938 A1 Aug. 20, 2015

Related U.S. Application Data

(60) Provisional application No. 61/941,254, filed on Feb. 18, 2014.

(30) Foreign Application Priority Data

Feb. 18, 2014 (EP) .................................... 14155656

(51) Int. Cl.
*A61F 2/44* (2006.01)
*A61B 17/80* (2006.01)
(Continued)

(52) U.S. Cl.
CPC ........ *A61F 2/4465* (2013.01); *A61B 17/8023* (2013.01); *A61B 17/7059* (2013.01);
(Continued)

(58) Field of Classification Search
CPC ....... A61B 17/8023; A61F 2002/30398; A61F 2/44; A61F 2002/443; Y10T 403/32491; F16B 7/18
(Continued)

(56) References Cited

U.S. PATENT DOCUMENTS 5,405,391 A * 4/1995 Hednerson ................ A61F 2/44
 623/17.15
5,964,762 A 10/1999 Biedermann et al.
(Continued)

FOREIGN PATENT DOCUMENTS

DE 20 2005 007 809 U1 7/2005
JP 11-506974 6/1999
(Continued)

OTHER PUBLICATIONS

European Search Report from European Application No. 14 155 656.3, European Search Report dated Jul. 17, 2014 and dated Jul. 24, 2014 (5 pgs.).

*Primary Examiner* — Brian E Pellegrino
(74) *Attorney, Agent, or Firm* — Lewis Roca Rothgerber Christie LLP (57) ABSTRACT

An implant for the application in spinal or trauma surgery is provided that has a variable axial length, the implant including a first member and a second member guided relative to the first member to be movable relative thereto in an axial direction for adjusting an overall length of the implant; and at least one engagement member that is in a first configuration configured to engage the first member and the second member such that the first member and the second member are locked with respect to each other and in a second configuration configured to engage the first member such that the second member is movable with respect to the first member; wherein, in the second configuration, the engagement member is configured to be secured against disengagement from the first member by an abutment, and wherein the engagement member is a monolithic part.

20 Claims, 6 Drawing Sheets

(51) Int. Cl.
*A61F 2/46* (2006.01)
*A61F 2/30* (2006.01)
*A61B 17/70* (2006.01)

(52) U.S. Cl.
CPC ..... *A61F 2/4611* (2013.01); *A61F 2002/3024* (2013.01); *A61F 2002/30148* (2013.01); *A61F 2002/30235* (2013.01); *A61F 2002/30367* (2013.01); *A61F 2002/30373* (2013.01); *A61F 2002/30405* (2013.01); *A61F 2002/30433* (2013.01); *A61F 2002/30507* (2013.01); *A61F 2002/30551* (2013.01); *A61F 2002/30556* (2013.01); *A61F 2002/30601* (2013.01); *A61F 2002/30622* (2013.01); *A61F 2002/30777* (2013.01); *A61F 2002/30784* (2013.01); *A61F 2002/30817* (2013.01); *A61F 2002/30818* (2013.01); *A61F 2002/4475* (2013.01); *A61F 2310/00017* (2013.01); *A61F 2310/00023* (2013.01); *A61F 2310/00071* (2013.01)

(58) Field of Classification Search
USPC .................................. 623/17.15; 606/289
See application file for complete search history.

(56) References Cited

U.S. PATENT DOCUMENTS

| | | | |
|---|---|---|---|
| 6,200,348 | B1 | 3/2001 | Biedermann et al. |
| 7,803,191 | B2 | 9/2010 | Biedermann et al. |
| 8,241,363 | B2 | 8/2012 | Sommerich et al. |
| 2005/0113921 | A1* | 5/2005 | An ............... A61F 2/44 623/17.11 |
| 2005/0177163 | A1* | 8/2005 | Abdou ........... A61B 17/8023 606/86 A |
| 2008/0039948 | A1* | 2/2008 | Biedermann ...... A61F 2/4637 623/17.16 |
| 2008/0177387 | A1* | 7/2008 | Parimore ......... A61F 2/30744 623/17.16 |
| 2009/0164018 | A1 | 6/2009 | Sommerich et al. |

FOREIGN PATENT DOCUMENTS

| | | |
|---|---|---|
| JP | 2008-18248 | 1/2008 |
| WO | WO95/20370 | 8/1995 |
| WO | WO 2007/137022 A2 | 11/2007 |
| WO | WO 2008/065450 A1 | 6/2008 |

* cited by examiner

LENGTH ADJUSTABLE IMPLANT

CROSS-REFERENCE TO RELATED APPLICATIONS

This application claims the benefit of U.S. Provisional Patent Application Ser. No. 61/941,254, filed on Feb. 18, 2014, and also claims priority to European Patent Application No. 14 155 656.3, filed on Feb. 18, 2014, the entire content of each of which is hereby incorporated by reference.

BACKGROUND

The invention relates to an implant that has a variable axial length and that is suitable for the application in spinal or trauma surgery. The implant includes a first member and a second member guided relative to the first member to be movable relative thereto in an axial direction for adjusting an overall length of the implant. Further, the implant includes an engagement member. In a first configuration, the engagement member is configured to engage the first member and the second member to lock the first member with respect to the second member. In a second configuration, the engagement member is configured to engage the first member but not the second member so that the second member is movable with respect to the first member. The engagement member is inhibited from disengaging from the first member.

An implant in the form of a length adjustable spacer for insertion between two vertebrae is known from U.S. Pat. No. 6,200,348 B1. The spacer comprises a first sleeve-shaped member and a second sleeve-shaped member which is slidably guided within the first member in an axial direction relative thereto for adjusting the overall length. The second member comprises on its outer surface facing the first member an axially extending portion having ratchet notches. The first member comprises an engagement member that cooperates with the ratchet notches for displacement to a desired overall length. The engagement member is formed by a tool that comprises a resiliently biased ball on its front face that is configured to engage the ratchet notches. After adjustment of the suitable axial lengthy a locking screw is used to lock the first and the second member relative to each other and the tool is removed.

Another spacer for insertion between two vertebrae is known from U.S. Pat. No. 7,803,191 B2. It comprises a first tubular member and a second tubular member. The length of the spacer is adjusted by telescoping the second tubular member out of the first tubular member using a tool and once the desired length is achieved, one or more locking screws are inserted to lock the second member relative to the first member.

A further length adjustable intervertebral spacer is known from. U.S. Pat. No. 8,241,363 B2. The spacer comprises a pair of coaxial annuluses locked together by an engagement member comprising a set screw and a pressure plate having an outer face contacting the set screw and an inner face having teeth adapted to mate with ratchet notches of the second member.

Another implant in the form of a length-adjustable bone plate is known from U.S. Pat. No. 5,964,762. In a similar manner as for the above described spacers, a first plate portion is slidably arranged relative to a second plate portion using a tool and the desired length is fixed with locking screws.

SUMMARY

According to an aspect of embodiments of the present invention, an implant for the application in spinal or trauma surgery that has a variable axial length is improved with respect to the safety of use and in terms of simplicity of the design.

Aspects and features of embodiments of the present invention are described herein with respect to some exemplary embodiments and are set forth in the claims.

An implant according to one or more embodiments of the present invention comprises a first member and a second member guided relative to the first member to be movable relative thereto in an axial direction for adjusting an overall length of the implant and an engagement member. In a first configuration, the engagement member is configured to engage the first member and the second member such that the first member and the second member axe locked with respect to each other. In a second configuration, the engagement member is configured to engage the first member such that the second member is movable with respect to the first member. In the second configuration, the engagement member is configured to be inhibited from disengaging from the first member by an abutment. The abutment prevents that a surgeon inadvertently screws out the engagement member completely. Therefore, during surgery, the engagement member cannot be disengaged from the first member and cannot become lost in a patient's body. This enhances the safety of the use of the implant.

The engagement member is a monolithic part, in particular in the simple form of a set screw that comprises a collar between a threaded portion and an engagement portion. The collar forms an abutment to prevent disengaging of the engagement member from the first member. Hence, the engagement member has a simple design and is easy to manufacture.

While engagement member is inhibited from escaping to the outside of the first member that faces away from the second member, it is also inhibited from escaping toward the side of the second member that is opposite to the first member because the engagement member is encased with at least a portion thereof between the first member and the second member. This also contributes to the safety of use.

BRIEF DESCRIPTION OF THE DRAWINGS

Further features and advantages of the present invention will become apparent from the description of some embodiments by means of the accompanying drawings. In the drawings:

FIG. 15b shows an enlarged view of a detail of FIG. 15a.

FIG. 15c shows an enlarged cross-sectional view of a portion of the implant according to FIG. 15a in an assembled state in a second configuration wherein the first member and the second member are movable relative to each other.

DETAILED DESCRIPTION

As can be seen from FIGS. 1 to 10, the implant according to the first embodiment is a spacer 1 for insertion between two vertebrae. The spacer 1 comprises a first tubular member 2 and a second tubular member 3. The first tubular member 2 and the second tubular member 3 are substantially cylindrical members. It should be noted, however, that the cylindrical shape is not necessary, but rather, any sleeve-like member with, for example, an oval, a kidney, a rectangular or square shape of the cross-section may be contemplated. An outer diameter of the second tubular member 3 is selected so as to allow a sliding guidance of the second tubular member 3 in the first tubular member 2. One or more engagement members 4 are provided for engaging and locking the first member 2 relative to the second member 3.

The first tubular member 2 has a first end 2a, an opposite second end 2b, a central longitudinal axis C and a hollow interior surrounded by the wall of the tube. In the wall of the tubular member, a plurality of openings is provided that serves tor allowing in-growth of blood vessels and tissue. For example, a plurality of circular openings 21a may be provided in an upper part of the first member 2 that is closer to the first end 2a. The circular openings 21a may be arranged in circumferential rows, wherein one row may be offset from the adjacent row. Similarly, a plurality of diamond- or square-shaped openings 21b may be present along the wall in a region closer to the second end 2b, also in rows, wherein one row is offset from another row. The last row of diamond-shaped openings 21b adjacent to the second end 2b may be cut along a circumferential line so that prongs 22 are formed that are configured to engage an end plate of a vertebral body. The prongs 22 may be sharpened to enhance the engagement. At the second end 2b, the first member 2 has a free end surface. An inner diameter of the first tubular member 2 in the region of the prongs 22 may be slightly enlarged compared to the diameter of the remaining part.

Figure 1:
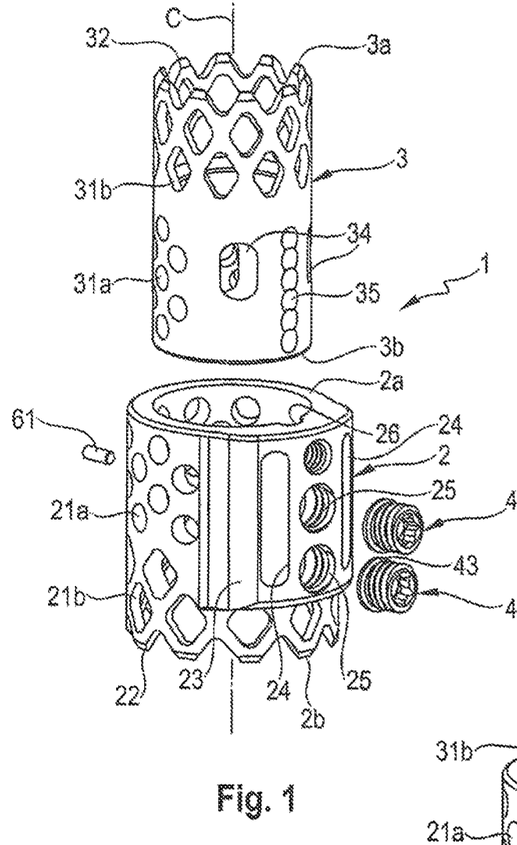
FIG. 1 shows a perspective exploded view of a first embodiment of an implant in the form of an intervertebral spacer.
Figure 3:
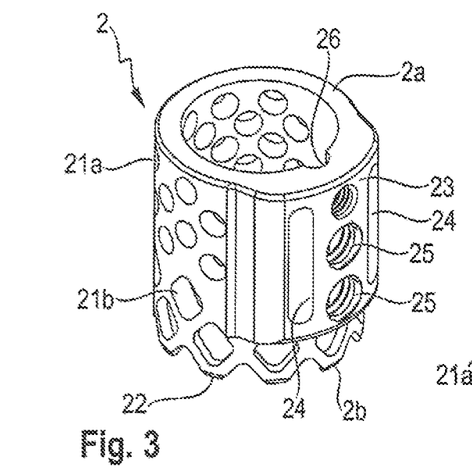
FIG. 3 shows a perspective view from above of a first member of the implant of FIGS. 1 and 2.
Figure 4:
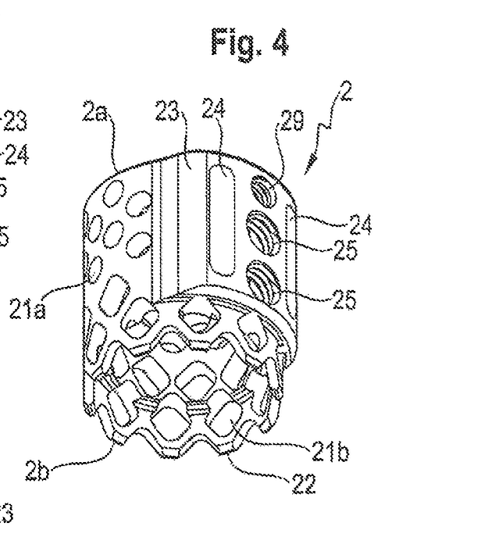
FIG. 4 shows a perspective view from below of the first member of the implant shown in FIGS. 1 to 3.

At one side of its outer surface, the first member 2 comprises a thickened portion 23 that may extend from the first end 2a along, for example, more than half of the axial length of the first member 2. In a circumferential direction, the thickened portion 23 may extend, for example, tip to one third of the circumference of the first member 2. A thickness of the second portion 23 in a radial direction is such that the one or more engagement members 4 can be accommodated in the wall of the thickened portion 23. However, the size of the thickened portion 23 is not limited to the size shown in the embodiment. It can be larger or smaller depending, for example, on the size and number of the engagement members.

Additionally, two elongate openings 24 are provided in the thickened portion 23 that extend from a distance from the first end 2a to a distance from the bottom end of the thickened portion 23 in an axial direction. The elongate openings 24 have an axial length that allows them to be engaged with a tool (not shown) that has scissor-like arms for telescoping the implant 1 when the second member 3 is slidably received in the first member 2. It shall be contemplated that only one elongate opening 24 is present or that there is no elongate opening and the telescoping of the second member 3 relative to the first member 2 is effected otherwise.

Between the elongate openings 24 one or more threaded holes 25 are provided that are spaced apart from each other in an axial direction and the centers of which are positioned on a line that is parallel to the central axis C. The threaded holes 25 serve for accommodating the engagement member 4 or a plurality of engagement members 4 corresponding to the number of threaded holes 25 that are adapted to receive the engagement member 4.

Figure 5:
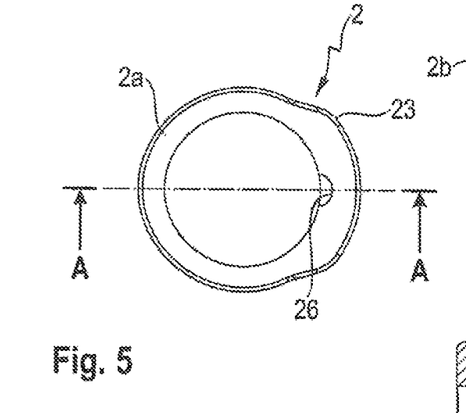
FIG. 5 shows a top view of the first member of FIGS. 3 and 4.
Figure 6:
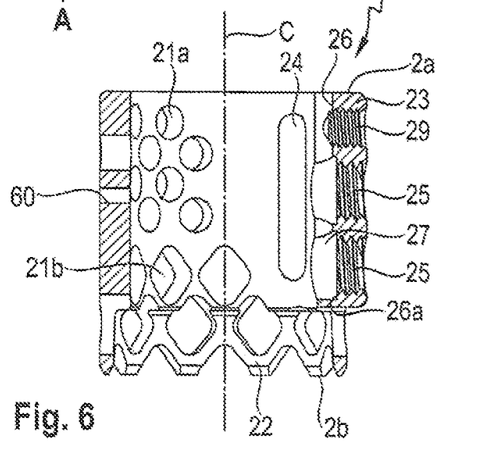
FIG. 6 shows a cross-sectional view of the first member of the implant shown in FIGS. 3 to 5, taken along the line A-A in FIG. 5.
Figure 7:
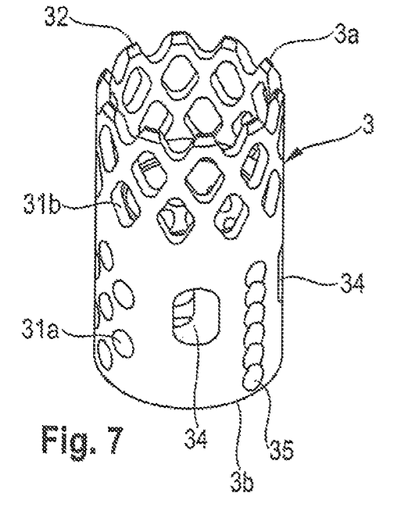
FIG. 7 shows a perspective view from above of a second member of the implant shown in FIGS. 1 and 2.
Figure 8:
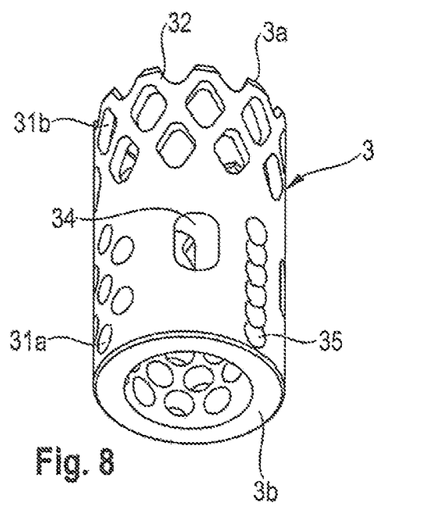
FIG. 8 shows a perspective view from below of the second member of the implant of FIG. 7.
Figure 9:
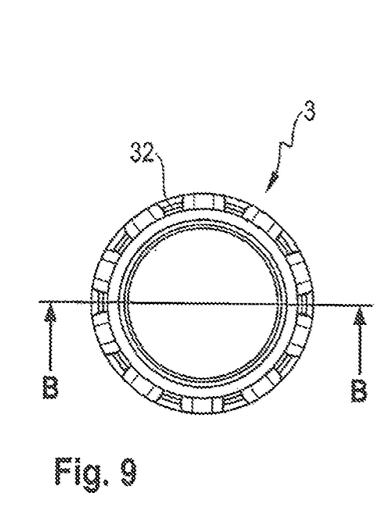
FIG. 9 shows a top view of the second member of FIGS. 7 and 8.

An axial recess 26, for example a cylinder-shaped recess, is provided in the inner wall of the thickened portion 23 at substantially the center thereof in a circumferential direction as best shown in FIG. 5. The recess 26 is open toward the top end 2a of the first member 2 and closed toward the lower end of the thickened portion 23. It provides space for an engagement portion of the engagement member 4 to extend therein and allows the engagement members 4 to be mounted into the first member 2 before the second member 3 is inserted into the first member 2. Furthermore, a recess 27 is present behind each of the threaded holes 25 so as to provide a larger inner diameter compared to that of the threaded hole 25. By means of this, an abutment 26a is formed that extends in an annular manner around die threaded hole 25. The abutment 26a has the function of cooperating with a portion of the engagement member 4 as described below. Moreover, by the recesses 27 a space is formed between the abutment 26a and an outer wall of the second tubular member 3. The dimension of the recesses 27 and of the axial recess 26 in a radial direction from the central axis C is such that the engagement members 4 can move from the threaded hole 25 toward the second member 3

Figure 15A:
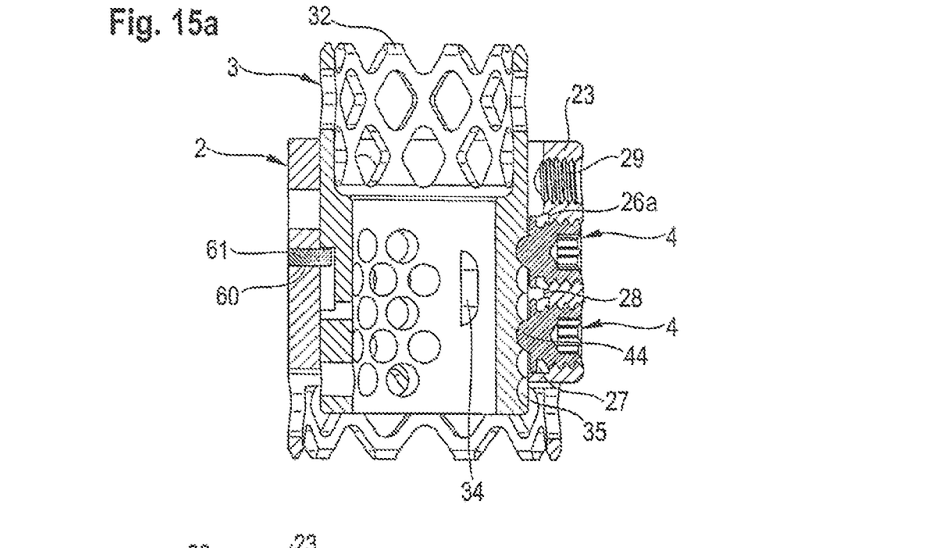
FIG. 15a shows a cross-sectional view of the intervertebral implant according to FIGS. 1 to 14 in a first configuration wherein the engagement member locks the first member and the second member with respect to each other, the cross-section taken in a plane along the central longitudinal axis of the implant.

Referring to FIG. 15a, the recesses 26, 27 of the thickened portion 23 form together with the outer wall of the second member 3 a compartment that encloses a portion of the engagement members 4, so that the engagement members 4 can also not escape to the inside of the spacer 1. It shall be noted, that small ridges 28 may be present in the inner wall of the thickened portion 23 to divide the compartment for the different engagement members 4.

In the embodiment shown, two threaded holes 25 are provided in an axial direction. It shall be noted, that only one single or more than two threaded holes may also be present. Optionally, there may be a further threaded hole 29 which is in the embodiment shown closest to the first end 2a and which may serve for a conventional locking screw or for another engagement member (not shown) which has smaller dimensions.

Referring again to FIG. 15a and, for example, FIG. 6, on a side opposite to the thickened portion 23, a small transverse through-hole 60 may be provided that serves for receiving a pin 61 that has a length so that one end thereof extends into the interior hollow portion of the first member 2 and into an elongate recess of the second member 3. The function of the pin 61 may be twofold. First, it maintains the alignment of the first member 2 and the second member 3 in a circumferential direction. Second, it may limit the overall length-adjustment so that a disengagement of the first member 2 and the second member 3 cannot occur.

Turning now to FIGS. 7 to 10, the second tubular member 3 has a first end 3a and an opposite second end 3b, a central axis C that coincides in the assembled state with the central axis C of the first member 2, a hollow interior and a wall defined by the tube. In the assembled state, the second end 3b faces toward the second end 2b of the first tubular member 2. The second member 3 also comprises a plurality of openings, wherein openings 31a of a first group may be circular and are arranged in rows offset from each other in a region closer to the second end 3b, and wherein openings 31b of a second group are substantially diamond-shaped or square-shaped and are arranged in a region closer to the first end 3a. Similar to the first tubular member 2, the second tubular member 3 comprises prongs 32 at the first end 3a that may be generated by cutting one row of the diamond-shaped openings 31b in the center so that the plurality of prongs 32 remain. The prongs 32 may be sharpened and serve for engagement with a vertebral end plate. At a distance from the second end 3b two circumferentially spaced apart elongate openings 34 are provided, the axial length of which is smaller than the axial length of the elongate openings 24 of the first member 2. The elongate openings 34 serve for engagement with the tool that distracts the second member 3 and the first member 2.

Figure 2:
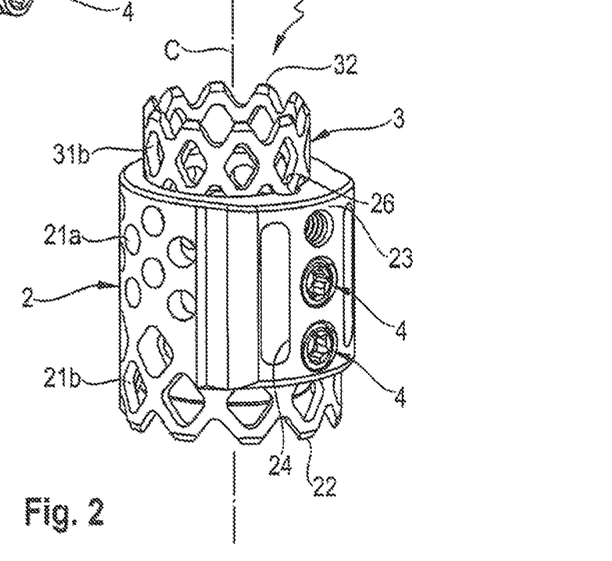
FIG. 2 shows a perspective view of the implant of FIG. 1 in an assembled state.

Between the elongate openings 34 an axial line of recesses 35 is provided in the outer wall of the second member 3. The recesses 35 are spherical segment-shaped and are arranged in a line parallel to the central longitudinal axis C of the spacer 1. Moreover, the recesses 35 are formed side by side and have a depth less than a radius thereof. In the assembled state, as shown in FIGS. 2 and 15a, the line of recesses 35 extends at least over the same length as the line of threaded holes 25. The line of recesses 35 forms a ratchet-like engagement portion on the second member 3 that cooperates with an engagement portion of the engagement member 4.

Figure 10:
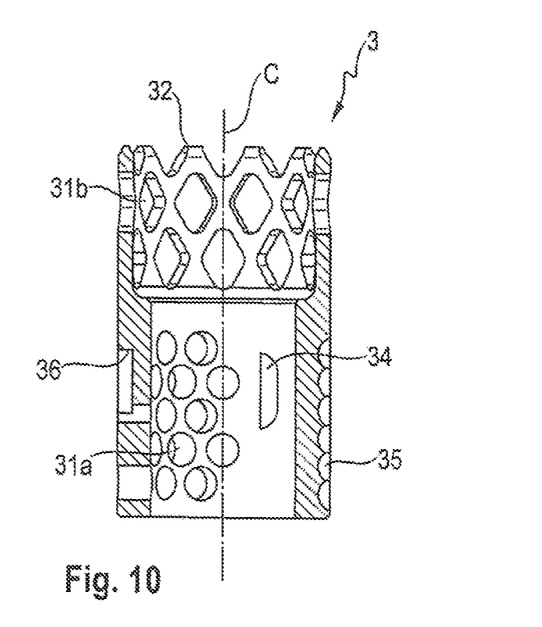
FIG. 10 shows a cross-sectional view of the second member of FIGS. 7 to 9, taken along the line B-B in FIG. 9.
Figures 11, 12, 13, 14:
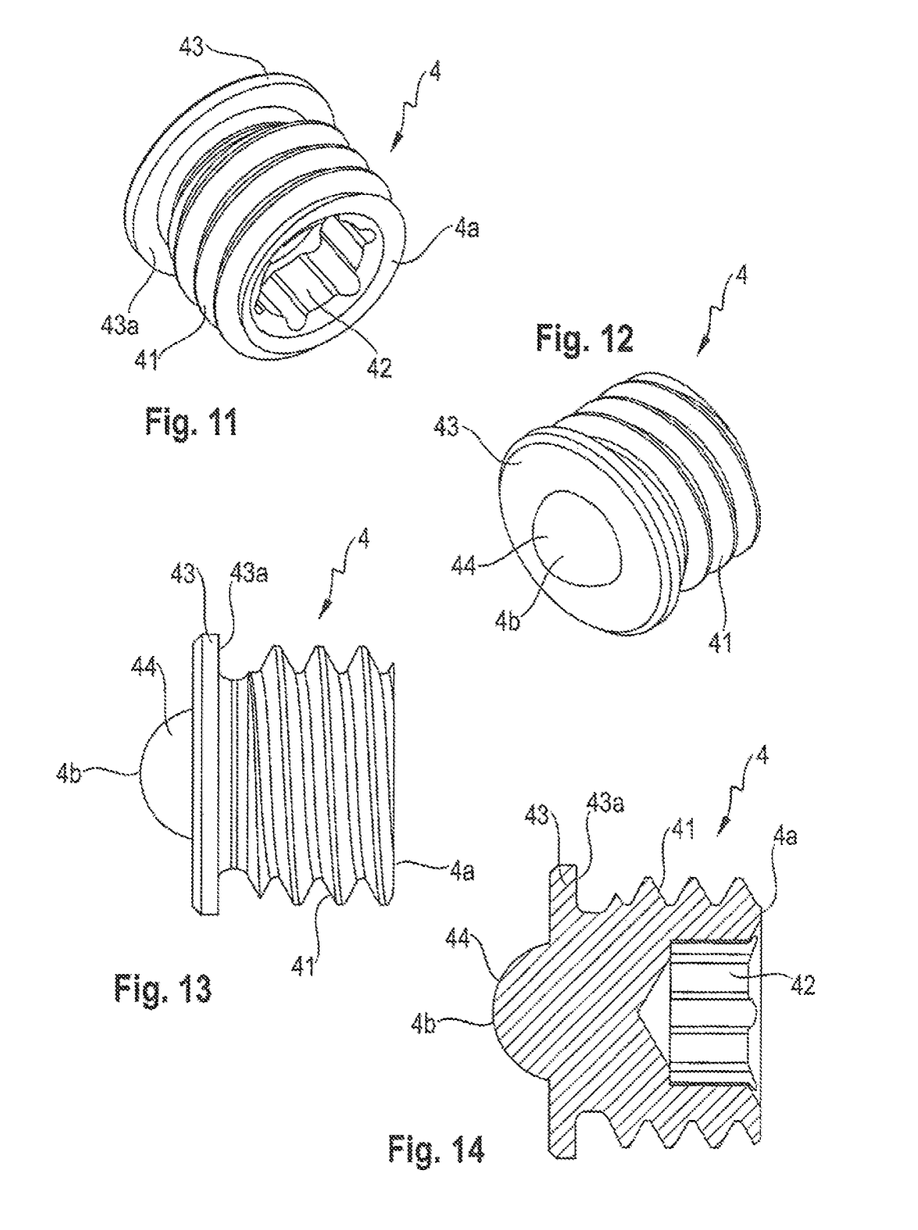
FIG. 11 shows a perspective view from above of an engagement member of the intervertebral implant shown in FIGS. 1 and 2.
FIG. 12 shows a perspective view from below of the engagement member of FIG. 11.
FIG. 13 shows a side view of the engagement member of FIGS. 11 and 12.
FIG. 14 shows a cross-sectional view of the engagement member of FIGS. 11 to 13, the cross-section taken in a plane along the screw axis.

As depicted in FIG. 10, on an opposite side of the line of recesses 35, an elongate recess 36 is formed in the outer wall of the second member 3 that does not extend completely through the wall. The elongate recess 36 serves for accommodating a front end of the pin 61 that is mounted into the pin hole 60 of the first member 2.

An inner diameter of the second member 3 in the region of the prongs 32 up to a distance from the first end 3a may be slightly larger than an inner diameter of the second member 3 in the region of the line of recesses 35.

Referring now to FIGS. 11 to 14, the engagement member 4 is a monolithic part that comprises a first end 4a and an opposite second end 4b. It is basically a set screw having a threaded first portion 41 adjacent to the first end 4a with an outer thread that cooperates with the inner thread of the threaded hole 25 of the first member 2. At the first end 4a, as common for set screws, an engagement recess 42 for a driver is provided. Between the first portion 41 and the second end 4b, a cylindrical collar 43 extends outward and beyond the threaded portion 41 in a radial direction. The collar 43 has an outer diameter that is greater than the outer diameter of the threaded portion 41.

A surface portion 43a of the collar 43 that faces toward the first end 4a serves as an abutment that cooperates with the abutment 26a in the inner wall of the thickened portion 23 of the first member 2. Between the collar 43 and the second end 4b of the engagement member, a spherical segment-shaped portion or ball-shaped projection 44 is provided that forms an engagement portion for engagement with the engagement portion that is provided by the axial line of recesses 35 in the second member 3. The engagement projection 44 fits into the spherical segment-shaped recesses 35 as illustrated in FIG. 15b.

Figures 15B, 15C:
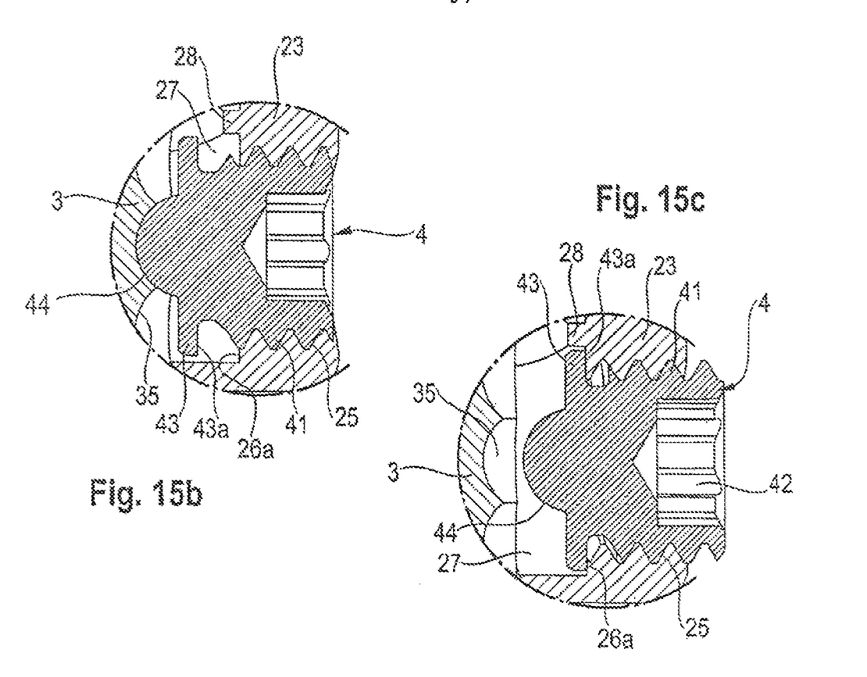

A total length of the engagement member 4 in a direction of the screw axis of the engagement member 4 is such that, as depicted in FIGS. 15b and 15c, in a first configuration the engagement projection 44 fits into the recesses 35 of the line of recesses in the second member 3 and the first end 4a is substantially flush with the outer surface of the thickened portion 23. However, the engagement member may also slightly project above the outer surface of the thickened portion 23. In a second configuration as depicted in FIG. 15c, the engagement member 4 abuts with the surface 43a against the abutment 26a provided in the inner wall of the thickened portion 23 and the engagement projection 44 is out of contact with the recesses 35. The threaded portion 41 may project out of the threaded hole 25. It shall be noted that it may be advantageous that the collar 43 extends fully around the screw axis, but it may also be sufficient, if the collar consists only of portions that have a limited extent in a circumferential direction but still fulfill the requirement of abutting against the abutment 26a.

All parts of the implant are made of a biocompatible metal, such as, for example, titanium or stainless steel, or of a biocompatible metal alloy, such as, for example, Nitinol. They may also be made from a biocompatible plastic material, such as, for example, polyetheretoerketone (PEEK). The parts may all be made of the same or of different materials.

The spacer 1 is assembled as follows. First, the engagement member 4 or the plurality of engagement members 4 are screwed from the inside of the first tubular member 2 with their threaded portion 41 into the threaded holes 25 so that the engagement projections 44 are accommodated in the recess 27, preferably, such that the collar 43 abuts with its surface 43a against the abutment 26a in the inner wall of the thickened portion 23. Thereafter, the second member 3 is inserted into the first member 2 in such a manner that the line of recesses 35 is aligned in a circumferential direction with the centers of the threaded holes 25 of the first member 2. Then, this position is secured by inserting the pin 61 into the pin-hole 60 until it engages the elongate recess 36 of the second member 3. By means of this, the first member 2 and the second member 3 are rotationally fixed with respect to each other. In the assembled state, the elongate holes 34 of the second tubular member 3 are in a circumferential direction aligned with the elongate holes 24 of the first tubular member 2.

In use, the spacer 1 may be filled with bone graft before inserting it between two vertebrae. For example, the spacer 1 is used to bridge the space after removal of a vertebra. The spacer 1 is inserted in a configuration where it has its minimum length. In this configuration, the first member 2 may be locked with respect to the second member 3. Then, the length of the spacer 1 is adjusted. First, the engagement members 4 are screwed slightly outward to move the engagement projections 44 out of the recesses 35 so that they no longer block a movement of the second member 3 relative to the first member 2. As shown in FIG. 15c, the engagement members 4 can be screwed out only to such an extent to which the collar 43 abuts against the abutment 26a. Therefore, an inadvertent screwing-out of the whole engagement member 4 is prevented and the engagement member 4 cannot become lost in the patient's body during surgery. Hence, a surgeon does not have to pay attention to carefully screw-out the engagement member. Also, because of the compartment formed between the inner wall of the thickened portion 23 and the outer wail of the second member 3, the engagement member 4 cannot escape to the inside of the spacer 1.

The length-adjustment is made using a tool that engages the elongate openings 24 and 34 of the first member 2 and the second member 3, respectively. The tool may be a tool with scissor-like arms that can be spread in the elongate opening and thereby distract the spacer 1.

When the desired length is achieved, the engagement members 4 are screwed towards the second member 3 again until the first configuration is achieved in that the engagement projection 44 engages the recesses 35 to block a further movement of the second member 3 relative to the first member 2.

Figure 16:
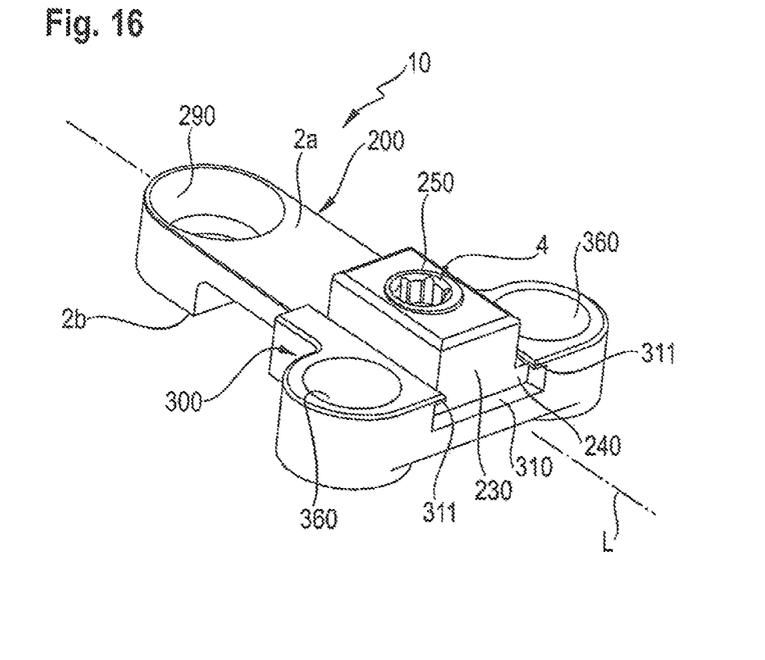
FIG. 16 shows a perspective view of a second embodiment of an implant in the form of a length-adjustable bone plate.
Figure 17:
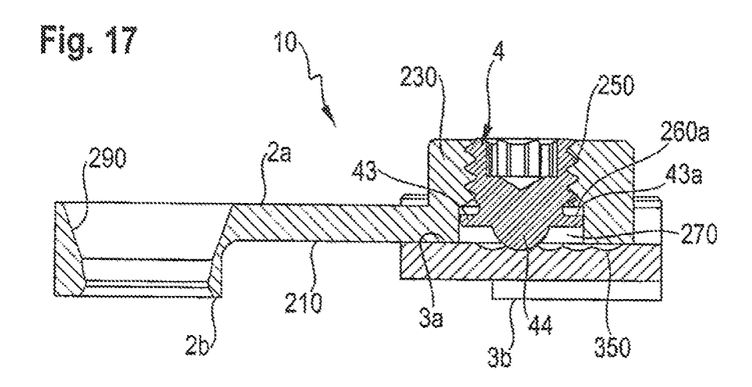
FIG. 17 shows a cross-sectional view of the implant of FIG. 16, the cross-section taken in a plane along the central longitudinal axis of the implant and wherein the implant is in a first configuration wherein the first member and the second member are locked with respect to each other.

A second embodiment in the form of a length-adjustable bone plate 10 will be explained referring to FIGS. 16 and 17. Parts and portions of the second embodiment that are identical or similar to that of the first embodiment are marked with the same reference numerals and the description thereof will not be repeated.

The bone plate 10 comprises a first member 200, a second member 300 that is guided with respect to the first member 200 such that the first member 200 is movable relative to the second member 300 in an axial direction. The axial direction is defined by a longitudinal axis L that forms a central axis of a guiding structure and tire main axis of the first member 200 or the second member 300. Furthermore, an engagement member 4 is provided that is identical to the engagement member of the first embodiment.

The first member 200 comprises a top side 2a and a bottom side 2b. In use, the bottom side 2b is oriented towards the bone surface and the top side 2a is facing away from the bone surface. The bottom side 2b may have a recessed surface portion 210 that may accommodate a portion of the second member 300 in such a manner that the second member 300 may be displaced in an axial direction substantially parallel to the bone surface with respect to the first member 200. At the top side 2a a thickened portion 230 may be provided that comprises a threaded hole 250 for receiving the engagement member 4 therein. The bottom side 2b may have in the area of the recessed portion 210 a further recess 270 extending away from a bottom surface of the recessed portion 210 to provide a space for accommodating the collar 43 and the engagement projection 44 of the engagement member 4 therein. An area around the threaded hole 250 forms an abutment 260a for the collar 43 of the engagement member. An outer contour of the thickened portion 230 may be substantially cuboid-shaped. At opposite sides projections 240 may be provided that can engage a guiding structure formed on the second member 300.

The first member 200 may further have one or a plurality of holes 290 that serve for the accommodation of heads of bone screws (not shown) therein for fixing the hone plate to the bone.

The second member 300 comprises a top side 3a and a bottom side 3b, wherein at least a portion of the bottom side has a surface that is substantially flush with the lowermost portion of the bottom side 2b of the first member 200. On the top side 3a, a groove 310 is provided that serves for guiding the first member 200 therein in an axial direction to allow the adjustment of the overall length of the bone plate. The groove 310 has small inwardly extending projections 311 on each side that extend slightly over the projections 240 so that the first member 200 is safely guided.

On the top side 3a, an axial line of spherical segment-shaped recesses 350 is provided. When the first member 200 and the second member 300 are assembled such that the lateral projections 240 are guided in the groove 310 and the engagement member 4 is inserted into the threaded hole 250, the line of recesses 350 is aligned in a transverse direction with the center of the threaded hole 250 such that the engagement portion 44 of the engagement member 4 can engage the recesses 350.

The second member 300 may also have one or more holes 360 extending from the top side 3a to the bottom side 3b for accommodating bone screws therein. It shall be noted that various different shapes may be contemplated for the first member and the second member. The shape is in any ease not limited to the shape shown in FIGS. 16 and 17.

In use, the engagement member 4 that has been. Inserted before assembly of the bone plate 10 into the threaded hole 250 of the first member 200 can assume two configurations. In a first configuration, shown in FIG. 17, the engagement member 4 is screwed towards the second member 300 until its engagement projection 44 engages one of the recesses of the line of recesses 350. In this configuration the first member 200 is locked with respect to the second member 300. In a second configuration, the engagement member 4 is screwed back until the collar 43 abuts against the abutment surface 260a provided at the inside of the inner wall of the thickened portion 230. The projection 44 is out of contact with the recesses 350 and die first member 200 can be displaced in the axial direction relative to the second member 300. The collar 43 prevents inadvertent disengagement of the engagement member 4 from the first member 200. This enhances the safety of use of the implant.

It shall be noted, that several engagement members 4 may be used. Further, as in the first embodiment, the collar 43 may be annular or may be provided only in circumferentially limited portions.

Modifications of the above described embodiments are conceivable. For example, the ratchet-like recesses may have a different shape as well as the engagement projection of the engagement member. The recesses do not need to have a circular shape but can be notch-like or otherwise shaped. The engagement projection of the engagement member may have any shape that is suitable to cooperate with the recesses.

It may also be contemplated that the engagement projections of the engagement member are spring-biased with regard to the remaining portions of the engagement member such that it may not be necessary to completely disengage the engagement projections from the engagement recesses when adjusting the length of the implant.

The first member and the second member may also be interchanged, so that the engagement member may be provided in the second member and the first member may have the engagement recesses.

What is claimed is:

1. An implant for application in spinal or trauma surgery having a variable axial length, the implant comprising:
   a first spacer member having a first end, an opposite second end, a longitudinal axis extending between the first end and the second end, and a first surface engageable with a bone;
   a second spacer member connectable to the first spacer member and configured to be guided relative to the first spacer member along the longitudinal axis for adjusting a distance between a free end of the second spacer member and the first surface of the first spacer member, wherein when connected, the first spacer member has a length greater than a length of the second spacer member in at least one of a direction along the longitudinal axis or a direction perpendicular to the longitudinal axis; and
   at least one engagement member configured to engage an opening in the first spacer member, the engagement member having a first end, an opposite second end, an abutment, between the first and second ends, and a first portion between the first end and the abutment for engaging the opening in the first spacer member, wherein the engagement member is a monolithic part, and wherein the abutment forms a collar having a width greater than a width of the opening in the first spacer member,
   wherein the implant is adjustable between a second configuration in which the first portion of the engagement member engages the opening in the first spacer member with the abutment contacting the first spacer member and being interposed in a compartment formed between a portion of the first spacer member and a portion of the second spacer member that overlap with one another while the second end of the engagement member is spaced apart from the second spacer member, such that the second spacer member is movable with respect to the first spacer member along the longitudinal axis and the engagement member is prevented from being removed from the opening in the first spacer member by the abutment, and a first configuration in which the first portion of the engagement member remains engaged with the opening in the first spacer and the engagement member is positioned closer to the second spacer member in a direction transverse to the longitudinal axis relative to the second configuration, such that the abutment is spaced apart from the first spacer member while the second end of the engagement member engages the second spacer member to axially lock the first spacer member and the second spacer member with respect to each other.

2. The implant of claim 1, wherein the engagement member further comprises a second portion that is configured to fit into an engagement portion of the second spacer member, wherein the abutment is located between the first portion and the second portion of the engagement member and configured to engage the first spacer member to prevent the engagement member from being removed from the first spacer member in the second configuration.

3. The implant of claim 1, wherein the opening in the first spacer member is a threaded hole, and wherein the engagement member is a set screw that is configured to engage the threaded hole in the first spacer member.

4. The implant of claim 3,
   wherein the first portion of the set screw comprises a threaded portion configured to engage the threaded hole of the first spacer member,
   wherein the set screw comprises an engagement projection for contacting the second spacer member in the first configuration, and
   wherein the collar of the abutment is between the threaded portion and the engagement projection, a greatest outer width of the collar being greater than an outer diameter of the threaded portion, to engage the first spacer member in the second configuration to prevent the set screw from being removed from the first spacer member.

5. The implant of claim 4, wherein the second spacer member comprises a series of recesses arranged along a direction of the longitudinal axis that are configured to be engaged by the engagement member in the first configuration.

6. The implant of claim 5, wherein the recesses are ratchet-like arranged recesses provided in an outer wall of the second spacer member in a line extending along a direction of the longitudinal axis.

7. The implant of claim 1, wherein an inner wall portion of the first spacer member and an outer wall portion of the second spacer member define the compartment that encloses the abutment of the engagement member.

8. The implant of claim 1, wherein the first spacer member is a sleeve-shaped part, and the second spacer member is a sleeve-shaped part that is insertable into a portion of the first spacer member and movable relative to the first spacer member along the longitudinal axis in the second configuration.

9. The implant of claim 8, wherein the implant is a spacer for insertion between two vertebrae.

10. The implant of claim 1, wherein the first spacer member is a plate-like part, and the second spacer member is a plate-like part.

11. The implant of claim 10, wherein the second spacer member comprises a groove for guiding the first spacer member.

12. The implant of claim 10, wherein the implant is a length adjustable bone plate.

13. The implant of claim 1, wherein the engagement member comprises a ball-shaped engagement portion.

14. A method of using an implant for application in spinal or trauma surgery including a first spacer member having a first end, an opposite second end, a longitudinal axis extending between the first end and the second end, and a first surface engageable with a bone, a second spacer member connectable to the first spacer member and configured to be guided relative to the first spacer member along the longitudinal axis for adjusting a distance between a free end of the second spacer member and the first surface of the first spacer member, wherein when connected, the first spacer member has a length greater than a length of the second spacer member in at least one of a direction along the longitudinal axis or a direction perpendicular to the longitudinal axis, and an engagement member configured to engage an opening in the first spacer member, the engagement member having a first end, an opposite second end, an abutment between the first and second ends, and a first portion between the first end and the abutment for engaging the opening in the first spacer member, wherein the engagement member is a monolithic part, and wherein the abutment forms a collar having a width greater than a width of the opening in the first spacer member, the method comprising: engaging the first surface of the first space member with a bone;

moving the second spacer member relative to the first spacer member along the longitudinal axis in a second configuration to adjust the distance between the free end of the second spacer member and the first surface of the first spacer member, wherein the first portion of the engagement member engages the opening in the first spacer member with the abutment contacting the first spacer member and being interposed in a compartment formed between a portion of the first spacer member and a portion of the second spacer member that overlap with one another while the second end of the engagement member is spaced apart from the second spacer member, and the engagement member is prevented from being removed from the opening in the first spacer member by the abutment; and engaging the second spacer member with the second end of the engagement member in a first configuration to axially lock the first spacer member and the second spacer member with respect to each other, wherein the first portion of the engagement member remains engaged with the opening in the first spacer member and the engagement member is positioned closer to the second spacer member in a direction transverse to the longitudinal axis relative to the second configuration, such that the abutment is spaced apart from the first spacer member.

15. The method of claim 14, wherein the opening in the first spacer member is a threaded hole, and wherein engaging the first spacer member with the engagement member comprises threadably engaging the engagement member in the threaded hole of the first spacer member.

16. The method of claim 14, wherein engaging the second spacer member with the engagement member comprises engaging an engagement projection of the engagement member in a recess of a series of ratchet-like arranged recesses of the second spacer member.

17. The method of claim 14, further comprising inserting the implant as a spacer between two vertebrae.

18. The method of claim 14, further comprising attaching the implant as a bone plate to a bone.

19. An implant for application in spinal or trauma surgery having a variable axial length, the implant comprising:

a first spacer member having a first end, an opposite second end, and a first surface engageable with a bone;

a second spacer member having a first end, an opposite second end, and a central axis extending through the first end and the second end and through a center of the second spacer member, wherein the second spacer member is connectable to the first spacer member and configured to be guided relative to the first spacer member along the central axis for adjusting a distance between the second end of the second spacer member and the first surface of the first spacer member, wherein when connected, the central axis extends through the first spacer member; and at least one engagement member having a first end, an opposite second end, and a first portion located closer to the first end than the second end for engaging the first spacer member, wherein the engagement member is positionable in an opening in the first spacer member, and wherein the engagement member is a monolithic part, wherein the implant is adjustable between a second configuration in which the the first portion of the engagement member engages the opening in the first spacer member while the second end of the engagement member is spaced apart from the second spacer member such that the second spacer member is movable with respect to the first spacer member along the central axis, and a first configuration in which the first portion of the engagement member remains engaged with the opening in the first spacer member and the engagement member is positioned closer to the second spacer member in a direction transverse to the central axis relative to the second configuration, such that the second end of the engagement member engages the second spacer member to axially lock the first spacer member and the second spacer member with respect to each other, and wherein a second portion of the engagement member having a width greater than the opening in the first spacer member is interposed in a compartment formed between portions of the first spacer member and the second spacer member that overlap with one another in both the first configuration and the second configuration to prevent the engagement member from being removed from the opening in the first spacer member, and wherein the second portion of the engagement member is between the first portion of the engagement member and the second end of the engagement member.

20. The implant of claim 1, wherein the free end of the second spacer member has a second surface engageable with a bone, and wherein the second spacer member is configured to be guided relative to the first spacer member along the longitudinal axis for adjusting a distance between the second surface of the second spacer member and the first surface of the first spacer member.

* * * * *

UNITED STATES PATENT AND TRADEMARK OFFICE
CERTIFICATE OF CORRECTION

PATENT NO. : 10,285,822 B2  
APPLICATION NO. : 14/624444  
DATED : May 14, 2019  
INVENTOR(S) : Timo Biedermann et al.

Page 1 of 1

It is certified that error appears in the above-identified patent and that said Letters Patent is hereby corrected as shown below:

In the Specification
| | |
|---|---|
| Column 1, Line 44 | delete "lengthy" and insert -- length, -- |
| Column 1, Line 56 | delete "from." and insert -- from -- |
| Column 2, Line 19 | delete "axe" and insert -- are -- |
| Column 2, Line 38 | delete "While" and insert -- While the -- |
| Column 3, Line 57 | delete "tor" and insert -- for -- |
| Column 4, Line 11 | delete "tip" and insert -- up -- |
| Column 4, Line 53 | delete "die" and insert -- the -- |
| Column 6, Line 49 | delete "polyetheretoerketone" and insert -- polyetheretherketone -- |
| Column 7, Line 23 | delete "wail" and insert -- wall -- |
| Column 7, Line 48 | delete "tire" and insert -- the -- |
| Column 8, Line 8 | delete "hone plate" and insert -- bone plate -- |
| Column 8, Line 33 | delete "ease" and insert -- case -- |
| Column 8, Line 35 | delete "been. Inserted" and insert -- been inserted -- |
| Column 8, Line 47 | delete "die" and insert -- the -- |

In the Claims
| | |
|---|---|
| Column 9, Line 27, Claim 1 | delete "abutment," and insert -- abutment -- |
| Column 9, Line 49, Claim 1 | delete "spacer" and insert -- spacer member -- |
| Column 10, Line 65, Claim 14 | delete "and the abutment" and insert -- and abutment -- |
| Column 11, Line 3, Claim 14 | delete "space" and insert -- spacer -- |
| Column 11, Line 16, Claim 14 | delete "member," and insert -- member -- |
| Column 12, Line 16, Claim 19 | delete "the the" and insert -- the -- |
| Column 12, Line 19, Claim 19 | delete "from the second" and insert -- from second -- |

Signed and Sealed this  
Nineteenth Day of May, 2020

Andrei Iancu  
*Director of the United States Patent and Trademark Office*